United States Patent [19]

Wells et al.

[11] Patent Number: 5,009,099

[45] Date of Patent: Apr. 23, 1991

[54] BACKGROUND CORRECTION METHOD FOR USE IN GAS CHROMATOGRAPHY

[75] Inventors: Gregory J. Wells, Suisun; Barbara A. Bolton, Albany, both of Calif.

[73] Assignee: Varian Associates, Inc., Palo Alto, Calif.

[21] Appl. No.: 349,201

[22] Filed: May 9, 1989

[51] Int. Cl.⁵ .................. G01D 18/00; G01N 21/73

[52] U.S. Cl. .................................. 73/1 G; 73/23.22; 356/307; 364/571.02

[58] Field of Search ........... 73/1 G, 23.1, 23.21–23.29, 73/23.35–23.42; 364/571.01–571.08; 422/89; 436/161; 356/307; 250/252.1 R, 252.1 A

[56] References Cited

U.S. PATENT DOCUMENTS

| 2,995,410 | 8/1961 | McDonnell et al. ............ 73/23.1 X |
| 3,257,847 | 6/1966 | Levy et al. ............................ 73/23.1 |
| 3,317,737 | 5/1967 | Köpsel et al. ..................... 356/307 |
| 3,381,519 | 5/1968 | Ashmead et al. ................... 73/23.1 |
| 3,468,156 | 9/1969 | Clerdy .............................. 73/1 G X |
| 3,531,202 | 9/1970 | Wilkinson et al. ............. 356/307 X |
| 3,646,331 | 2/1972 | Lord .............................. 364/571.04 |
| 3,895,803 | 7/1975 | McLean et al. .................... 356/307 |
| 4,151,739 | 5/1979 | Brener et al. ....................... 73/1 G |
| 4,575,241 | 3/1986 | Demers et al. ................ 356/307 X |
| 4,645,342 | 2/1987 | Tanimoto et al. ............. 356/307 X |
| 4,852,384 | 8/1989 | Woolbert et al. ................... 73/1 G |

FOREIGN PATENT DOCUMENTS

| 1075033 | 4/1980 | Canada ............................. 356/307 |
| 36788 | 3/1979 | Japan ............................... 356/307 |
| 6158 | 1/1981 | Japan ............................... 436/161 |
| 155339 | 9/1983 | Japan ............................... 356/307 |
| 7410464 | 2/1976 | Netherlands ..................... 356/307 |
| 1105914 | 7/1984 | U.S.S.R. ......................... 364/571.05 |

OTHER PUBLICATIONS

"Application of Gas Chromatography to Microdetermination of Carbon and Hydrogen"; *Analytical Chemistry*; vol. 32, No. 2, Feb. 1960, pp. 274–277; O. E. Sundberg et al.

"A Modulator for the Automatic Subtraction of Continuous Background in Optical Spectrometers"; *Optics and Spectroscopy*; Feb. 1964; vol. 16, No. 2, pp. 184–186; G. M. Svishchev.

"A Method of Background Correction for Direct Reading Optical Emission Spectroscopic Trace Analysis Using Offset Exit Slits"; *Analytical Chemistry* vol. 41 No. 2, Feb. 1969; pp. 396–398; John A. Leys.

"Wavelength Modulation for Background Correction in Graphite Furnace Atomic Emission Spectroscopy"; *Applied Spetroscopy*; vol. 30, No. 3, 1976; pp. 324–329; M. S. Epstein et al.

K. S. Brenner, entitled "Practical Experience with a Microwave Plasma Detector: Limits of Measurement and Examples of Applications," *Journal of Chromatography*, 167 (1978), pp. 365–380.

A. Bolla–Kamara, et al., "Considerations in the design of a microwave induced plasma utilizing the $TM_{010}$ cavity for optical emission spectroscopy", Spectrochimica Acta, vol. 36B, No. 10, pp. 973–982, 1981.

R. K. Skogerboe, et al., "A Dynamic Background Correction System for Direct Reading Spectrometry", Applied Spectroscopy, vol. 30, No. 5, pp. 495–500, Sept.–Oct. 1976.

*Primary Examiner*—Tom Noland
*Attorney, Agent, or Firm*—Stanley Z. Cole; David Schnapf

[57] ABSTRACT

A method of correcting for background changes in a plasma emission detector comprising a photodetector array is disclosed. In the photodetector array a plurality of sensors are used to detect the emission lines from a discrete number of selected elements including carbon. It is shown that, to the first order, there is a correlation between the response at detectors other than the carbon detector with the response at a carbon detector. The exact extent of this correlation is highly dependent on the amount of nitrogen present in the carrier gas used in the system. A calibration curve can be generated which allows compensation at a frequency of interest as a function of the magnitude of the carbon signal. This curve will depend on the level of nitrogen in the carrier gas and can be empirically determined each time a new bottle of gas is connected to the system. In a preferred embodiment, the calibration curve is not referred to unitl the carbon response reaches a preselected threshold value corresponding to the point on the calibration curve where there is a measurable spurious reading.

3 Claims, 3 Drawing Sheets

BACKGROUND CORRECTION METHOD FOR USE IN GAS CHROMATOGRAPHY

BACKGROUND OF THE INVENTION

This invention is in the field of gas chromatography and is specifically related to background correction means useful with plasma emission detectors for analyzing the output of a gas chromatograph (GC).

In gas chromatography a sample of interest is volatilized and injected into a gas chromatography column, typically housed in an oven. A carrier gas flows constantly through the column sweeping the sample along with it. Differential adsorption and desorption of the sample constituents on the partition medium in the column separates the sample into its components. Having been thus separated, the constituents of the sample elute from the column at different times and flow to a detector which continuously measures one or more properties of the gas eluting from the column. A change in the properties being measured relative to the baseline property of the carrier gas signifies that a sample constituent is passing through the detector. This is commonly referred to as a "peak". A recording of the detector signal, which may contain a large number of peaks, is called a chromatogram.

A variety of detectors are available to the chromatographer. The selection of what type of detector to use is a function of a variety of factors including the type(s) of samples being investigated, cost, sensitivity, selectivity and others. Some detectors respond well to a broad variety of sample species while others are useful for only specific types of compounds.

One type of detector which has gained increasingly widespread attention for use in gas chromatography is the plasma emission detector. In a plasma emission detector sample eluting from the GC column is introduced into a high temperature atmospheric pressure plasma where the sample molecules are broken up by action of the thermal energy into atomic or molecular fragments and ionized. As the species are swept through the plasma they undergo energy transitions and emit characteristic light spectra. Sample identification can be made by monitoring the wavelengths and intensities of the light so emitted. The plasma emission detector has been shown to be a highly sensitive universal detector. Microwave energy may be used to generate the plasma in this type of detector, which may then be called a microwave emission detector or "MED".

As a practical matter, a select discrete group of light frequencies is monitored in a plasma emission detector. (For purposes of this disclosure the term "light" should be understood to mean not only the visible portion of the electromagnetic spectrum, but also the infrared and ultraviolet.) These frequencies correspond to the characteristic emission wavelengths of certain sample species, generally elements, of the greatest interest. When a sample component of interest enters the plasma and is excited a signal is generated in the detector associated with the characteristic wavelength. Unfortunately, light at that characteristic frequency may be generated in the absence of the particular element or compound of interest thereby interfering with the analysis. This will be referred to as "background" radiation or light. One type of such background radiation will be a low level of general background radiation emitted from the plasma across a broad spectrum in the absence of any sample. In addition, other sample constituents in the plasma, particularly molecular fragments, may have complex emission spectra with lines (i.e., frequencies) near the line of interest. In gas chromatography of organic compounds this problem is particularly severe in the spectral region between 600 nm and 1000 nm where the formation of cyanide (CN) results in large increase in the background due to molecular band emissions in this region of the spectrum.

Prior art devices have utilized such techniques as increased resolution, wavelength modulation and locating a reference detector near the line of interest to correct for emissions not associated with the element of interest. Each of these techniques has its disadvantages however. Increasing the resolution, i.e., narrowing the frequency band which will generate a respond in the detector by using, for example, a narrow band filter, will help minimize interferences associated with nearby emission lines. But his occurs at the expense of absolute sensitivity for the line of interest. When the background noise is due to factors other than flicker in the light source, the noise will remain constant as the resolution is changed, so the effect of increasing resolution is to decrease sensitivity and, thus, signal-to-noise ratio.

In wavelength modulation, the signal to the detector is alternately moved between the intensity maximum and a point away from the maximum. Assuming that the underlying background signal remains at a constant level throughout the wavelength region of interest, the resulting signal has a constant contribution from the background and an amplitude modulated contribution due to the line emission. Using well-known techniques it is then easy to extract the modulated portion of the signal, thereby eliminating the background contribution. However, this techniques also results is decreased sensitivity and reduced signal-to-noise ratio.

In some instances, a reference detector is used to monitor changes in the background, and these changes are substracted from the signal at the wavelength of interest. However, this approach assumes that changes to the background at the reference detector are the same as the changes at the line of interest. This correlation often does not exist. In addition, depending on the physical construction of the detector apparatus, it may be difficult or impossible to locate a reference detector close enough to the detector for the wavelength of interest.

Accordingly, it is an object of this invention to compensate for changes to the background radiation at a wavelength of interests in a plasma emission detector used in a gas chromatography system to improve the quantitative and qualitative reliability of detection at said wavelength.

Another object of this invention is to provide a low-cost, first-order background correction method for use with a plasma emission detector connected to a gas chromatograph.

Yet another object of this invention is to provide a method of correction for background variations caused by the presence of carbon compounds in a sample under analysis.

SUMMARY OF THE INVENTION

These and other objects are realized in the present invention comprising a method of correcting for fluctuations in the background spectrum in a plasma emission detector used for the analysis of organic compounds. The method of the present invention relies on the fact that, to the first order, most of the large background fluctuations at certain wavelengths are due to the presence of CN in the sample which is, in turn, related to the levels of carbon and nitrogen. In this invention, measurements are made to arrive at a calibration curve which relates the detector response at a frequency of interest to the carbon response. The calibration curve is related, in large degree, to the amount of nitrogen in the carrier gas, and needs to be adjusted whenever there is a change in the nitrogen level in the carrier gas. The data comprising the calibration curve is stored in memory and is used to make adjustments to the signal levels at the frequency of interest as a function of the carbon response.

DETAILED DESCRIPTION

Figure 1A:
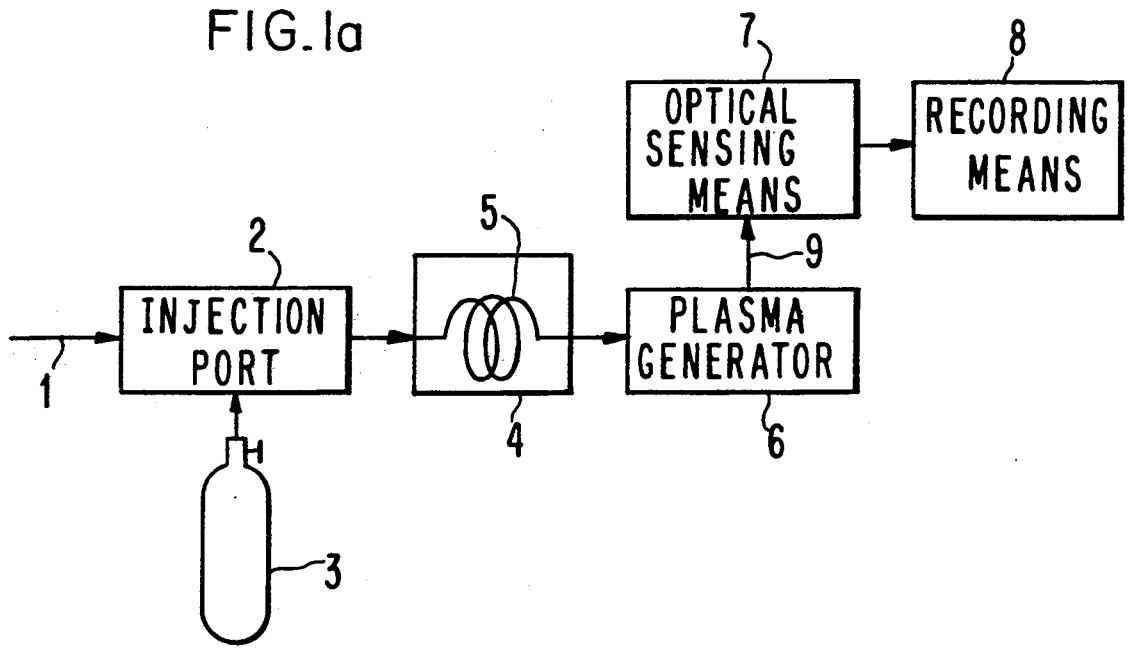
FIGS. 1a and 1b shows schematic representations of a gas chromatography system with an emission detector using a photodetector array.
Figure 1A:
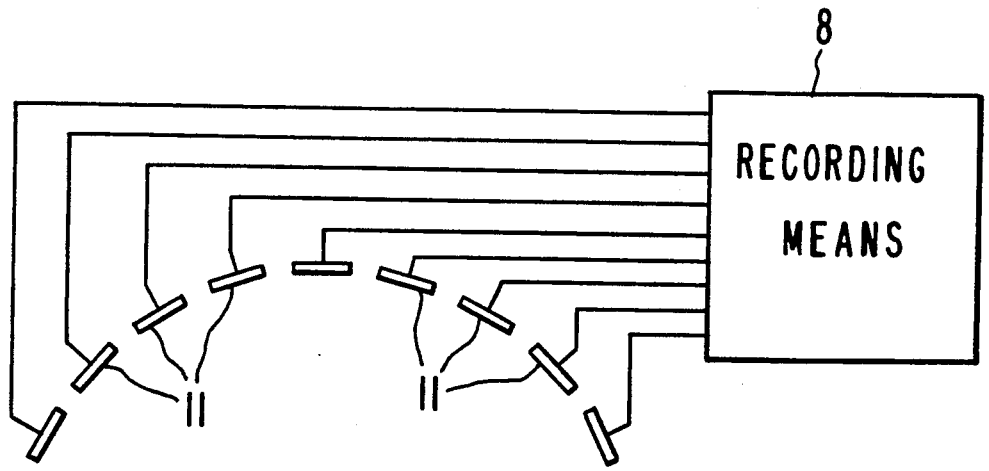

FIG. 1(a) is a schematic representation of a gas chromatography system of the type which may be used to practice the present invention. A sample 1 is introduced into the system by means of an injection port 2 where it is mixed with a carrier gas from supply 3 and swept into gas chromatography column 4 typically housed in an oven 5. The sample is separated into its constituent components by action of the column 4, and the resulting peaks, spaced apart temporally, elute from the column swept by the carrier gas and into a plasma generator 6. As it enters the plasma the sample is broken down into atoms and molecular fragments which are excited and emit light at wavelengths characteristic of the species in the plasma. Light which is so emitted is detected by optical sensing means 7 and a signal from the detecting means is sent to recording means 8 which can be a chart recorder, a computer memory or any other of a number of well known devices.

Figure 1B:
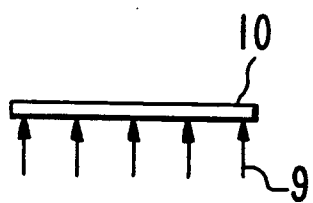

FIG. 1(b) is a simplified schematic representation of an optical sensing means 7 which may be used to practice the present invention. Light 9 of various wavelengths emitted from the plasma is separated by a diffraction grating 10 or other similar means and is dispersed at angles which correspond to particular wavelengths. An array of detectors 11, which may be photodiodes or other light sensors, are located in positions which correspond to the wavelengths of interest to the chromatographer. For example, detectors may be positioned at angles corresponding to the wavelengths of the principal emission lines of carbon, iodine and sulfur. Thus, when an iodine containing compound is swept into the plasma generator 6, the iodine atoms will emit light at said principal emission line, and the light so emitted will fall on the "iodine" detector (i.e., photodiode) by action of diffraction grating 10 and causing a responsive signal in the sensor. Each of the photodiodes is connected to the input of recording means 8 so that the instantaneous signal from the detector can be measured and recorded.

Figure 2:
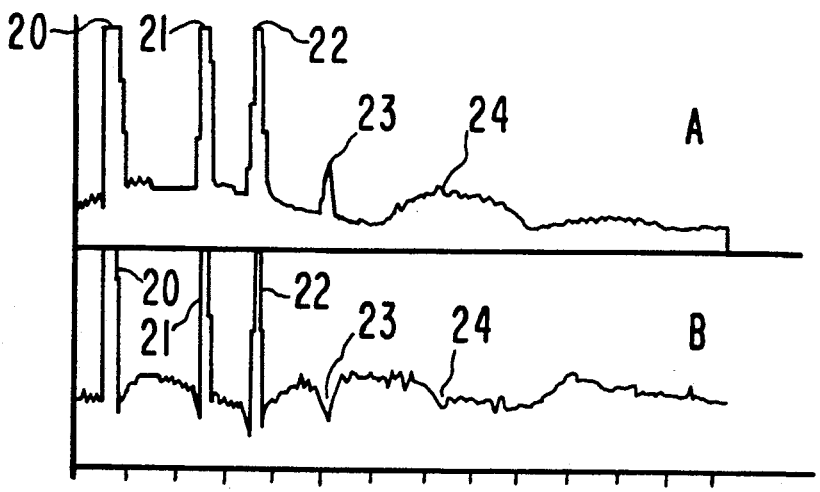
FIG. 2 shows two chromatograms on a single time axis of the signal at the iodine wavelength of a sample mixture comprising various organic compounds but no iodine.

Following the above example further, a problem arises for the interpretation of the chromatographic data, however, when an element or compound other than iodine emits light at or sufficiently near the iodine wavelength to cause a spurious response at the "iodine" detector. FIG. 2 shows two chromatograms of the signal at the iodine detector for a sample mixture consisting solely of hydrocarbons absent any iodine. In particular the sample mixture contained five alkanes (peaks 21-25) and a solvent (peak 20). In the FIG. 2(a) chromatogram the carrier gas (helium) is contaminated by 5 parts per million (ppm) of nitrogen, while in the FIG. 2(b) chromatogram nitrogen is at the 0.1 ppm level. While it is readily apparent that the nitrogen level in the carrier gas correlates to the magnitude of the spurious response at the iodine detector, as a practical matter it would be prohibitively expensive to use a helium carrier gas completely uncontaminated by nitrogen.

Insofar as gas chromatography is typically used to analyze sample mixtures containing organic compounds, and insofar as helium is typically used as the carrier gas in a gas chromatography system comprising a plasma emission detector, both carbon and nitrogen will be ubiquitous in the such a detector. In the detector elemental carbon and nitrogen form CN, which emits light at many lines in the spectral region between 600 nm and 1000 nm. These emissions create the types of spurious peaks shown in FIG. 2. In the present invention it is assumed, to the first order, that any organic molecule which enters the plasma consists entirely of carbon.

Figure 3A:
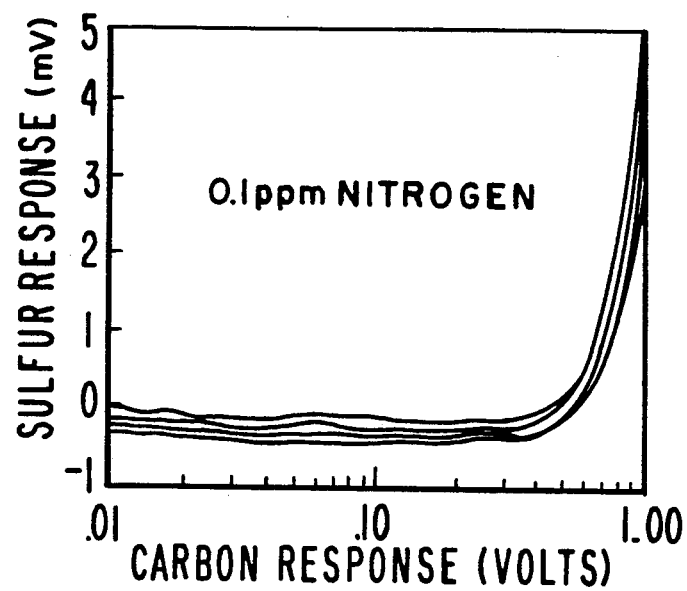
FIGS. 3a and 3b shows two plots of the detector response at the sulfur wavelength as a function of the response at the carbon wavelength and nitrogen concentration.
Figure 3B:
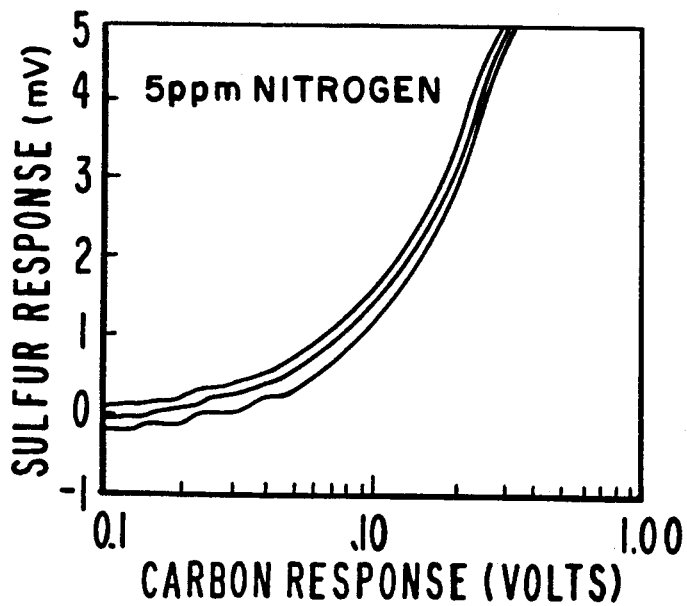

FIG. 3 shows plots of the response at the sulfur wavelength as a function of the response at the carbon wavelength. FIG. 3(a) shows plots for the same five alkanes shown in the FIG. 2 chromatograms, with nitrogen contamination of the carrier gas at 0.1 ppm, while FIG. 3(b) shows plots for the same five alkanes with carrier gas contamination at 5 ppm. It can be seen that each of the hydrocarbons produces essentially the same plot, and that the exact shape and magnitude of the response is, to the first order, entirely dependent on the amount of nitrogen contamination of the helium carrier gas.

In the present invention, the general response curve of FIG. 3 is used as a calibration curve for the purpose of removing the background response as a function of the carbon response. It is seen from FIG. 3 that the calibration curve is a function of the level of nitrogen contamination. In the preferred embodiment the calibration curve is empirically determined every time there is a change in the level of nitrogen contamination of the helium used in the system. Initially, therefore, it is necessary to acquire and store data which relates the response at any given detector of interest to the carbon response. This may be accomplished as explained above in respect to FIG. 3. Thereafter, this stored data will be used to correct readings at each said detector as a function of the response at the carbon detector.

It can be seen from FIG. 3 that for small amounts of carbon there will be little, if any, change in the background at the sulfur detector. In a preferred embodiment of the present invention the system is programmed so that no adjustment is made to the signal at the detector of interest until the carbon response reaches a threshold value. Normally, the threshold will be selected to correspond to the point on the calibration curve where the response at the selected detector is measurably different than zero. When the carbon response goes above this threshold, the signal from the detector of interest is adjusted in accordance with the calibration curve stored in memory to compensate for background changes due to the carbon response. Of course it is necessary to generate a calibration curve for each detector of interest, i.e., each detector which is subject to background radiation from carbon and nitrogen. With the widespread availability of compact memory and microprocessor integrated circuits these functions can be accomplished readily with programming and circuitry well within the capabilities of those skilled in the art.

In the present invention, the response at the carbon detector is continuously measured and recorded. In the preferred embodiment, nothing is done to the signal from the detector of interest until the carbon response reaches a certain threshold, the threshold value being determined from the calibration curved stored in memory and corresponding to a point on the curve where the response at the detector of interest differs from zero by a preselected amount. At each point in time when the carbon response exceeds the threshold, a calculation is performed from the data in memory comprising the calibration curve and the calculated amount is substracted from the signal at the detector of interest to compensate for the carbon contribution to the signal. This can be accomplished either in real time as the measurements are made or after storing the raw data from the sensors in system memory.

In an alternative embodiment, no threshold value for referring to the calibration curve is used and, instead, a calculation of compensation is made at each time point. Of course, for carbon levels which are low the compensation amount will normally be zero.

As noted above, the presence of nitrogen in the helium carrier gas supply is highly correlated to the shape of the calibration curve. At the present time, in the preferred embodiment for practicing the present invention a new calibration curve is empirically developed each time there is a change in the level of nitrogen contamination of the helium carrier gas. As a practical matter this only occurs when a new bottle of helium is connected to the system. The method described above in respect to the preferred embodiment requires the generation of a two-dimensional curve (carbon response vs. response at the detector of interest) for each value of nitrogen. Carrying this forward, once sufficient data is collected, it is possible to generate a three dimensional surface correlating the nitrogen level, the carbon response, and the response at the detector of interest, i.e., the surface lies in a three dimensional space where one axis is the nitrogen level, another axis the carbon response, and the third axis is the response at the detector of interest. Once this data is collected, it can be stored in system memory. Thereafter, a calibration curve can be generated by the system computer whenever a new source gas is connected by simply measuring the level of nitrogen in the gas.

The first order approximation described above relates the background changes solely to the presence of CN. However, it is noted that other elements, particularly oxygen and silicon, form carbon compounds which may contribute to changes in the background and for which correction can be made. More than one mechanism may be responsible for variation in the background. These may be either negative or positive changes. Negative changes may be due to suppression of the background continuum in certain spectral regions as sample is introducted into the plasma. Since many of these effects are related to the ionization potential of the elements in the sample, and since most elements typically found in organic compounds have nearly the same ionization potential (i.e., between 10 and 12 electron volts (ev)) in comparison to helium (21.5 ev), it has been observed that the changes in background are correlated to the carbon response. For most elements these are second order effects. However, oxygen has a persistent background line emission because it is impossible to fully eliminate it as a contaminant in the system. When carbon is introduced CO is formed suppressing the background oxygen emission. Again, the correction for these elements will in any case correlate to the carbon response. An advantage of using empirically generated calibration curves lies in the fact that they will include necessary adjustments due to the contribution of each of these elements and for other effects and can be used so long as there is no substantial change in any of the elements after the curve is created.

Figure 4:
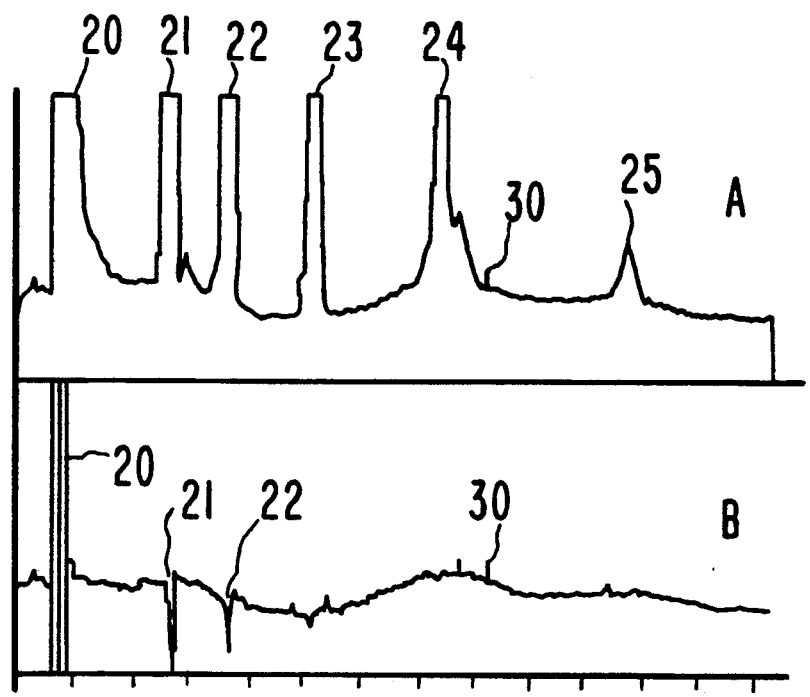
FIG. 4 shows two chromatograms on a single time axis of the signal at the sulfur wavelength with and without background correction in accordance with the present invention.

FIG. 4 shows two chromatograms of the response at the sulfur detector for the same sample mixture of alkanes described above. (Likewise, the peaks are numbered as described above.) The FIG. 4 (a) chromatogram shows the uncompensated detector response while the FIG. 4(b) chromatogram shows same data after background correction in accordance with the present invention. It should be noted that this method does not correct for baseline changes, so that the noise spike 30 appears in both chromatograms. Thus, the noise in the signal is not increased by this technique. In the FIG. 4(b) chromatogram the calibration curve was created by means of a series of straight line fits to selected points on the FIG. 3 plot. This method is least accurate at the high carbon response levels where the curvature of the plot is greatest, resulting in incomplete removal of the background at the highest peaks. Clearly, other well known techniques, such as cubic splines, least squares, polynomial, etc., can be used to generate more accurate calibration curves in regions of high curvature.

Figure 5:
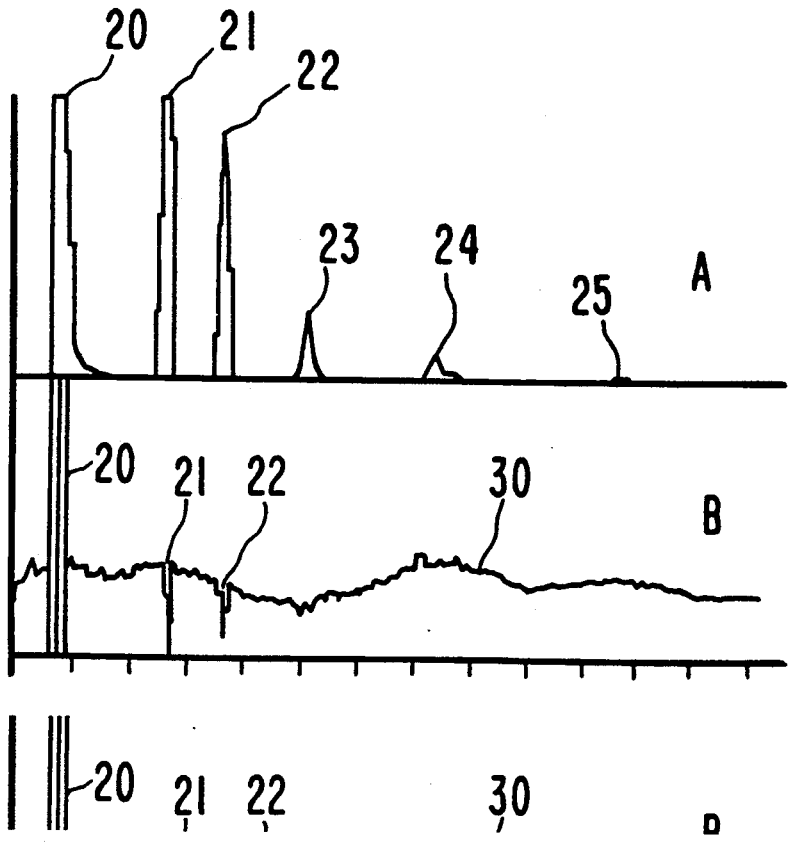
FIG. 5 shows two chromatograms on a single time axis, one at the carbon wavelength and the other at the sulfur wavelength with background correction in accordance with the present invention.

Finally, FIG. 5 shows a chromatogram of the response at the carbon detector along side the chromatogram, corrected in accordance with the present invention, at the sulfur detector for the same five alkanes. (Note that FIG. 5(b) and FIG. 4(b) are the same. However, the scale for the FIG. 5(a) chromatogram is three orders of magnitude greater than that of the sulfur chromatogram.)

Since many changes could be made in the above method and many apparently widely different modifications and embodiments of this invention can be made without departing from the scope thereof, it is intended that all matter contained in the above description or shown in the accompanying drawings shall be interpreted as illustrative and not in a limiting sense.

What is claimed is:

1. A method of correcting for changes in background radiation in a plasma emission detector comprising a plurality of sensors associated with specific emission frequencies including a sensor associated with at least one principal carbon emission frequency and another sensor associated with a frequency of emission of another element, each time a new source of helium is connected to the system generating a calibration curve which correlates the response at the said other sensor in the absence of the other element of interest with the response at said carbon sensor, storing said calibration curve in system memory, thereafter, measuring the signal response at said carbon sensor, simultaneously measuring the signal response at said other sensor, subtracting from the signal from said other sensor an amount determined from the calibration curve stored in said system memory.

2. A method of correcting for changes in background radiation in a plasma emission detector comprising a plurality of sensors associated with specific emission frequencies including a sensor associated with at least one principal carbon emission frequency and another sensor associated with a frequency of emission of another element, generating a calibration curve which correlates the response at the said other sensor in the absence of the other element of interest with the response at said carbon sensor by plotting the response at the sensor of interest in the absence of the element associated with that sensor against the response at the carbon sensor, storing said calibration curve in system memory, thereafter, measuring the signal response at said carbon sensor, simultaneously measuring the signal response at said other sensor, subtracting from the signal from said other sensor an amount determined from the calibration curve stored in said system memory.

3. A method of correcting for changes in background radiation in a plasma emission detector comprising a plurality of sensors associated with specific emission frequencies including a sensor associated with at least one principal carbon emission frequency and another sensor associated with a frequency of emission of another element, generating a calibration curve which correlates the response at the said other sensor in the absence of the other element of interest with the response at said carbon sensor, storing said calibration curve in system memory, thereafter, measuring the signal response at said carbon sensor, simultaneously measuring the signal response at said other sensor, subtracting from the signal from said other sensor an amount determined from the calibration curve stored in said system memory, wherein the generation of said calibration curve comprises the step of measuring the nitrogen content of the carrier gas used in the system.

* * * * *